United States Patent [19]

Kruger et al.

[11] 4,181,517

[45] Jan. 1, 1980

[54] 1,2,3-THIADIAZOLE-2-ID DERIVATIVES, PROCESS FOR MAKING THE SAME AND COMPOSITION CONTAINING THE SAME HAVING A GROWTH REGULATING ACTIVITY FOR PLANTS

[75] Inventors: Hans-Rudolf Kruger; Reinhart Rusch; Friedrich Arndt, all of Berlin, Fed. Rep. of Germany

[73] Assignee: Schering Aktiengesellschaft, Berlin and Bergkamen, Fed. Rep. of Germany

[21] Appl. No.: 897,858

[22] Filed: Apr. 19, 1978

[30] Foreign Application Priority Data

Apr. 28, 1977 [DE] Fed. Rep. of Germany ....... 2719810

[51] Int. Cl.$^2$ ............... A01N 9/12; C07D 285/06; C07F 3/00; C07F 3/06
[52] U.S. Cl. ............................................ 71/73; 71/76; 71/82; 71/90; 544/64; 544/134; 544/225; 544/226; 544/331; 544/327; 546/12; 546/209; 546/277; 546/11; 548/127; 548/109
[58] Field of Search ......... 260/299, 306.8 D, 270 PD, 260/293.68; 71/72, 76, 90 (U.S. only), 73, 82; 544/64, 134, 225, 328, 331; 546/2, 209, 277, 11

[56] References Cited

U.S. PATENT DOCUMENTS

| | | | |
|---|---|---|---|
| 3,565,901 | 2/1971 | Cebalo | 260/293.4 |
| 3,787,434 | 1/1974 | Volpp et al. | 260/306.8 D |
| 3,883,547 | 5/1975 | Schulz et al. | 260/306.8 D |

*Primary Examiner*—Alton D. Rollins
*Assistant Examiner*—Diana G. Rivers
*Attorney, Agent, or Firm*—Michael J. Striker

[57] ABSTRACT

1,2,3-Thiadiazole-2-id-derivative of the formula

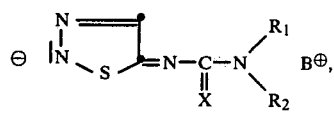

in which $R_1$ is hydrogen or alkyl which may be substituted in one or several places by oxygen or sulfur and wherein $R_1$ has the meaning as given in the attached specification and wherein X is oxygen or sulfur and B is a univalent metal atom. The compounds have properties suited for controlling the natural growth and natural development of plants and in addition have a superior defoliating property.

19 Claims, No Drawings

1,2,3-THIADIAZOLE-2-ID DERIVATIVES, PROCESS FOR MAKING THE SAME AND COMPOSITION CONTAINING THE SAME HAVING A GROWTH REGULATING ACTIVITY FOR PLANTS

BACKGROUND OF THE INVENTION

The invention relates to 1,2,3-thiadiazole-2-id-derivatives.

Herbicidal agents on the basis of carbamoylaminothiadiazoles are already known, for instance 2-(N,N-dimethylcarbamoylamino)-5-methylthio-1,3,4-thiadiazole (Swiss Pat. No. 502,762). These are agents which result in complete destruction of the undesirable plants.

Aliphatic thiophosphates are also known as agents for causing defoliation of plants, for instance tri-n-butyltrithiophosphate (U.S. Pat. No. 2,954,467).

This latter compound has not always an adequate activity. Besides, it results in developing unpleasant odors which sometimes annoy the party using it.

It is therefore an object of the present invention to provide for an agent for the control of the natural growth and development of plants which also has a superior defoliant action.

SUMMARY OF THE INVENTION

The invention resides in a 1,2,3-thiadiazole-2-id-derivative of the formula

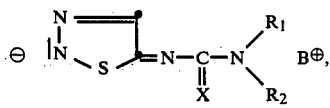

in which $R_1$ is hydrogen or alkyl which may also be substituted in its chain in one or several places by oxygen or sulfur and wherein $R_2$ is (a) alkyl which may be substituted in one or several places in its chain by oxygen or sulfur, (b) a cycloaliphatic hydrocarbon reside which may be substituted in one or several places by alkyl, (c) an aromatic hydrocarbon residue which may be substituted in one or several places by alkyl, halogen, alkylthio, alkoxy, trifluoromethyl and/or nitro, (d) a heterocyclic hydrocarbon residue which contains at least one nitrogen atom in its ring and which may also be substituted, or (e) wherein $R_1$ and $R_2$ together with the adjoining nitrogen atom form a morpholino-, piperidino- or pyrrolidino group, and wherein X is oxygen or sulfur and B is a univalent metal equivalent.

The invention also embraces a process for making the compounds and compositions containing the same.

The compounds of the invention have superior growth regulating and developing properties for plants.

This natural growth regulation of the compounds of the invention results in a morphological modification of the plant which can easily be determined by visual observation. These changes may consist in the size, the shape or the color of the plant or any parts thereof.

The effects obtained can generally be designated as retardation. It is believed that the compounds have an effect on the hormone supply of the plants.

In certain kinds of plants this development results in a reduction or obliteration of the apex growth whereby a shorter main stalk or stem and a delayed lateral branching is obtained. These modifications of the natural growth result in smaller, more bushy plants.

The use of the compounds of the invention therefore has surprising technical advantages. Thus, the compounds delay the vegetative growth of the plants which in case of agricultural plants is very often desirable. In addition, it is possible to obtain desirable effects with the plants, as for instance defoliation, increased formation of off-shoots, and a shortening of the axial members.

With many plants such as potatoes, sugarcane, sugar beet, grapes, melons, fruit trees and silage plants, it is possible, together with the suppression of the apical growth, to obtain an increase even of the carbohydrate contents of the plants as harvested. In the case of fruit and plantation cultures the inhibition of the plant growth on the other hand results in shorter more sturdy twigs, so that the branches are better accessible and the harvesting process if facilitated. In case of grasses there is principally obtained an inhibition of the vertical growth which permits further spacing of the times for mowing operations.

One of the specific effects of the invention is the defoliation. It is known among experts that defoliation is not a herbicidal action. Destruction of the treated plants may occur if the leaves still stick to the dead plant and the productive plant parts are damaged. The goal of the defoliation, to obtain an easier harvesting operation and a harvested product of greater purity, thus could be defeated. It is therefore necessary that the plant remains alive while the leaves separate and drop to the ground. This furthermore permits a further development of the productive plant parts which will prevent a new leaf growth.

The compounds of the invention can preferably be used in mixture with prior art compounds or by successive application therewith. Such prior art compounds are for instance:

auxin,
α-(2-chlorophenoxy)-propionic acid,
4-chlorophenoxyacetic acid
2,4-dichlorophenoxyacetic acid,
indolyl-3-acetic acid,
indolyl-3-butyric acid,
α-naphthyl acetic acid,
β-naphthoxy acetic acid,
naphthylacetamide,
n-m-tolylphthalamido acid,
gibberellins,
S,S,S-tri-n-butyl-trithiophosphoric acid ester,
cytokinines,
2-chloroethylphosphonic acid,
2-chloro-9-hydroxyfluorene-9-carboxylic acid,
2-chloroethyl-trimethylammoniumchloride,
N,N-dimethylaminosuccinic acid amide,
2-isopropyl-4-dimethylammonio-5-methylphenyl-piperidino-1-carboxylic acid estermethylchloride,
phenyl-isopropylcarbamate,
3-chlorophenyl-isopropylcarbamate,
ethyl-2-(3-chlorophenylcarbamoyloxy)-propionate,
maleic acid hydrazide,
2,3-dichloroisobutyric acid,
di-(methoxythiocarbonyl)disulfide,
1,1'-dimethyl-4,4'-bipyridylium-dichloride,
3,6-endoxohexahydrophthalic acid,
3-amino-1,2,4-triazole,
1,2,3-thiadiazolyl-5-yl-urea derivative, 1-(2-pyridyl)-3-(1,2,3-thiadiazole-5-yl)-urea
2-butylthio-benzthiazole,
2-(2-methylpropylthio)-benzthiazole,
3,4-dichloroisothiazole-5-carboxylic acid,
2,3-dihydro-5,6-dimethyl-1,4-dithiino-1,1,4,4-tetroxide,
arsenic acid,
cacodylic acid,
chlorates, preferably calcium chlorate, potassium chlorate, magnesium chlorate or sodium chlorate,
calcium cyanamide,
potassium iodide,
magnesium chloride,
abscisinic acid,
nonanol,
N,N-bis(phosphonomethyl)glycine, or
N-(phosphonomethyl)-glycine-monoisopropylamino salt.

The activity and speed of action of the compounds can furthermore also be increased by activity increasing additives such as organic solvents, wetting agents and oils. This permits a further reduction of the amounts of the active compounds proper.

The compounds of the invention are preferably used in the form of compositions such as powders, spraying agents, solutions, emulsions or suspensions. There are added liquid and/or solid carrier materials or diluents and, if desired, wetting agents, adhesion promoting agents, emulsifiers and/or dispersants.

Suitable liquid carrier materials are for instance water, aliphatic and aromatic hydrocarbons, like benzene, toluene, xylene, cyclohexanone, isophorone, dimethylsulfoxide, dimethylformamide, and furthermore mineral oil fractions.

As solid carrier materials there are suited mineral earths, for instance tonsil, silicagel, talc, kaolin, attaclay, limestone, silicic acid and plant products such as flours.

There may also be added surface active agents as for instance calcium lignosulfonate, polyoxyethylenealkylphenylether, naphthalenesulfonic acids, and their salts, phenolsulfonic acids and their salts, formaldehyde condensation products, fatty alcohol sulfates as well as substituted benzosulfonic acids and their salts.

The proportion of active agents in the different compositions may be varied widely. The compositions may for instance contain about 10 to 80% by weight of active agents, 90 to 20% by weight of liquid or solid carrier materials and, if desired, up to 20% by weight of surface active agents in which case the carrier materials should be subject to a corresponding reduction in amounts.

The weight ratio of the individual active agents when used in mixtures with other agents of the prior art should be between about 100:1 and 1:1000, preferably between 10:1 and 1:100. It depends on the sensitivity and the strength of the plants, the time of application and the climatic conditions and ground composition.

The amounts for regulating the growth of the plants in case of a surface treatment are usually 0.05 to 5 kg of active agent per about 2.5 acres. In specific cases it is possible to exceed these limits upwards or downwards. The manner of growth regulating action depends also on the time of treatment, the type of plants and the concentration.

The compounds of the invention can be applied to different parts of the plants such as the harvested mass, the roots, the stems, the leaves, the blossoms, and the fruits. It is also possible to apply the compounds by spraying in a preemergence or postemergence application. As against various weeds the inhibiting effects may be such that a total obstruction of the development including bushes occurs.

DETAILS OF THE INVENTION AND PREFERRED EMBODIMENTS

Among the compounds of the invention those are preferred in which in the above formula I $R_1$ is hydrogen or alkyl with 1 to 4 carbon atoms, for instance methyl, ethyl, isopropyl, propyl, butyl, and in which $R_2$ is hydrogen or alkyl of 1 to 4 carbon atoms, for instance methyl or ethyl, cycloalkyl of 5 to 8 carbon atoms, for instance cyclopentyl, cyclohexyl, methylcyclohexyl, aryl, for instance, phenyl, halogenophenyl, $C_1$-$C_4$ alkylphenyl, $C_1$-$C_4$ alkoxyphenyl, nitrophenyl, trifluoromethylphenyl, or is a pyridyl or pyrimidyl residue which may be substituted in one or several positions by the same or several substituents selected from the group consisting of $C_1$-$C_4$ alkyl, $C_1$-$C_4$ alkoxy, halogen, nitro and trifluoromethyl, and wherein B is an alkali metal atom, preferably lithium, sodium or potassium or a corresponding equivalent amount of a bivalent atom, e.g. Zn, Mn, Ca, Mg or Ba, and wherein X is oxygen or sulfur.

Compounds of the invention with superior action are, for instance, 5-(phenylcarbamyolimino)-1,2,3-thiadiazoline-2-id, potassium salt;
5-(phenylcarbamoylimino)-1,2,3-thiadiazoline-2-id, sodium salt;
5-(phenylcarbamoylimino)-1,2,3-thiadiazoline-2-id, lithium salt;
5-(phenylcarbamoylimino)-1,2,3-thiadiazoline-2-id, calcium salt;
5-(methylphenylcarbamoylimino)-1,2,3-thiadiazoline-2-id, sodium salt;
5-(methylphenylcarbamoylimino)-1,2,3-thiadiazoline-2-id, potassium salt;
5-(methylphenylcarbamoylimino)-1,2,3-thiadiazoline-2-id, lithium salt;
5-(2-pyridylcarbamoylimino)-1,2,3-thiadiazoline-2-id, sodium salt;
5-(2-pyridylcarbamoylimino)-1,2,3-thiadiazoline-2-id, potassium salt; and
5-(2-pyridylcarbamoylimino)-1,2,3-thiadiazoline-2-id, lithium salt.

PROCESS OF MAKING

The compounds of the invention can for instance be made by reacting (1,2,3-thiadiazole-5-yl)-urea of the formula

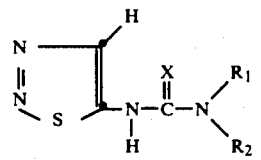

II with a metal compound of the formula ti B Y    III

The reaction may be effected in a solvent. $R_1$, $R_2$, X and B in the above formula have the same meaning as in the previously given formula I, and Y is hydrogen, hydroxyl, lower alkoxy or amino.

The reaction may be carried out at a temperature between 0° and 120° C., but preferably is carried out at room temperature. The reactants are used in about equimolar amounts. As reaction media there may be used polar organic solvents alone or in mixture with water or also water alone. The selection of the solvents or suspension agents depends on the type of the metal compound B Y.

As solvents or suspension agents there may for instance be used the following: water, acid nitriles, like acetonitrile, ethers, like tetrahydrofuran and dioxane, alcohols, like methanol, ethanol and isopropanol, and acid amides, like dimethylformamide.

The salts of the invention when made from bivalent metals which have a low solubility in water, preferably are produced from aqueous solutions of the alkali salts of the invention to which highly soluble salts of the corresponding bivalent metals are added, such as salts of calcium chloride, calcium acetate and zinc acetate.

The isolation of the formed compounds of the invention in case of low soluble compounds is effected by filtration. In case of compounds having better solubility the isolation is accomplished by distilling the compounds off the solvents at normal or reduced pressure or by precipitation with less polar organic solvents, for instance ketones or ethers. As a matter of convenience one can proceed by mixing the corresponding 1,2,3-thiadiazole-5-yl-urea derivatives with the particular metal hydroxides, preferably by employing an excess of hydroxide, and then using the mixtures in the form of the resulting water soluble spray masses.

The following examples illustrate the making of the compounds:

EXAMPLE 1

5-(phenylcarbamoylimino)-1,2,3-thiadiazoline-2-id, sodium salt.$H_2O$ 11.0 g (0.05 mol) of 1-phenyl-3-(1,2,3-thiadiazole-5-yl)-urea, m.p.: 213° C. (decomposed) were added rapidly to a solution of 2 g (0.05 mol) of sodium hydroxide in 50 ml water while stirring at room temperature. After continued stirring for 30 minutes an almost clear solution was obtained which after filtration at 50° C. was subjected to concentration in a vacuum. The residue was dried in a vacuum at 50° C. The yield was 11.5 g=91.5% of the calculated value. The product was in the form of colorless crystals having a melting point >270° C. (decomposed).

EXAMPLE 2

5-(phenylcarbamoylimino)-1,2,3-thiadiazoline-2-id, calcium salt.8 $H_2O$ 22.0 g (0.1 mol) of 1-phenyl-3-(1,2,3-thiadiazole-5-yl)-urea were added to a solution of 4 g (0.1 mol) sodium hydroxide in 300 ml water at room temperature. The almost clear solution obtained as in Example 1 was subjected to filtration and then reacted with a solution of 8.8 g (0.05 mol) of calciumacetatemonohydrate in 100 ml water. Stirring was continued at room temperature for another hour. The formed crystals were removed by suction and dried at 50° C. in a vacuum. The yield was 25.5 g=82% of the calculated value. The compounds were in the form of colorless crystals having a melting point of >300° C.

The following compounds were made in an analogous manner.

| Compound No. | Name of Compound | Physical Constants |
|---|---|---|
| 3 | 5-(phenylcarbamoylimino)-1,2,3-thiadiazoline-2-id, potassium salt x $H_2O$ | m.p.: >205° C. (decomposed) |
| 4 | 5-(phenylcarbamoylimino)-1,2,3-thiadiazoline-2-id, lithium salt x 4 $H_2O$ | m.p.: >270° C. (decomposed) |
| 5 | 5-(methylphenylcarbamoylimino)-1,2,3-thiadiazoline-2-id, sodium salt x $H_2O$ | m.p.: >200° C. (decomposed) |
| 6 | 5-(methylphenylcarbamoylimino)-1,2,3-thiadiazoline-2-id, potassium salt x $H_2O$ | m.p.: >120° C. (decomposed) |
| 7 | 5-(methylphenylcarbamoylimino)-1,2,3-thiadiazoline-2-id, lithium salt x HO | m.p.: >180° C. (decomposed) |
| 8 | 5-(2-pyridylcarbamoylimino)-1,2,3-thiadiazoline-2-id, sodium salt x 1.5 $_2O$ | m.p.: >200° C. (dicomposed) |
| 9 | 5-(2-pyridylcarbamoylimino)-1,2,3-thiadiazoline-2-id, potassium salt x $H_2O$ | m.p.: >180° C. (decpomposed) |
| 10 | 5-(2-pyridylcarbamoylimino)-1,2,3-thiadiazoline-2-id, lithium salt x $H_2O$ | m.p.: >230° C. (decomposed) |
| 11 | 5-(phenylthiocarbamoylimino)-1,2,3-thiadiazoline-2-id, sodium salt x $H_2O$ | m.p.: 135° C. (decomposed) |
| 12 | 5-(phenylcarbamoylimino)-1,2,3-thiadiazoline-2-id, magnesium salt x $H_2O$ | m.p.: 325° C. |
| 13 | 5-(phenylcarbamoylimino)-1,2,3-thiadiazoline-2-id, zinc salt x 3 $H_2O$ | m.p.: 208° C. (decomposed) |
| 14 | 5-phenylcarbamoylimino-1,2,3-thiadiazoline-2-id, manganese salt x 3 $H_2O$ | m.p.: 250° C. (decomposed) |
| 15 | 5-phenylcarbamoylimino-1,2,3-thiadiazoline-2-id, barium salt x 3 $H_2O$ | m.p.: 250° C. (decomposed) |

The compounds of the invention are salts corresponding to the following limit formulae:

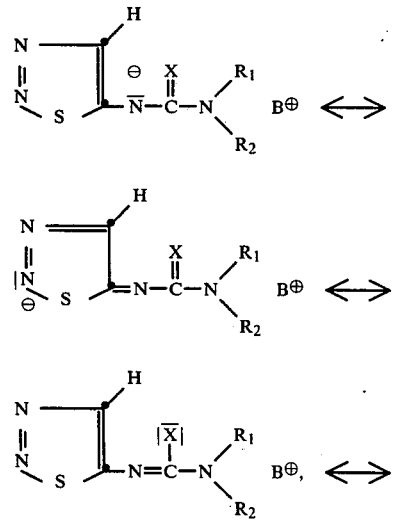

or more generally

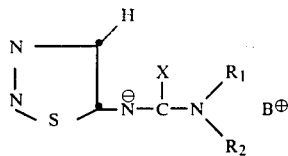

To simplify the expression these different formulas were not expressed in the general formula I.

The compounds of the invention are colorless and nonsmelling crystalline bodies.

The alkali salts have a high solubility in water, a good solubility in polar organic solvents like sulfoxides, for instance dimethylsulfoxide; in lower alcohols, for instance methanol and ethanol; in carboxylic acid amides, for instance, dimethylformamide. They are less soluble in carboxylic acid nitriles, for instance acetonitrile and they are virtually insoluble in hydrocarbons, halogenated hydrocarbons and ethers. The corresponding salts of bivalent metals have a reduced water solubility but they are still well soluble in dimethylsulfoxide, dimethylformamide and methanol.

The compounds of the invention are easily coupled with solvents and they are normally isolated as solvates, for instance as hydrates or alcoholates.

The following examples will further illustrate the activity and use of the compounds:

EXAMPLE 3

In a hothouse potted bushbeans (*Phaseolus vulgaris*) after formation of the primary leaves and soybeans (*Glycine maxima*) at the inception of the development of the first trilobe leaf were treated as appears from the table below with different amounts of active agents (0.1 and 3 kg of active agent per about 2.5 acres). The agents applied appear from the table below. The application was effected by first forming a 20% spray powder which then was applied in an aqueous suspension with an amount of liquid of 500 liters per about 2.5 acres. The growth regulating effect was determined two weeks after treatment by measuring the length of the first internodium. The results of the measurements are then related to the untreated control plants and are calculated according to their percent growth delay.

As appears from the following table a growth regulating effect can be obtained with the compounds of the invention across a broad range of concentrations without causing any burn damages in the leaves.

TABLE I

| Compound of the Invention | Amount kg/about 2.5 acres | growth delay in % | |
|---|---|---|---|
| | | bushbean | soybean |
| 5-(phenylcarbamoylimino)-1,2,3-thiadiazoline-2-id, sodium salt × H$_2$O | 0.1 | 30 | 25 |
| | 0.3 | 65 | 70 |
| 5-(phenylcarbamoylimino)-1,2,3-(thiadiazoline2-id, calcium salt × 8 H$_2$O | 0.1 | 35 | 25 |
| | 0.3 | 55 | 65 |
| 5-(phenylcarbamoylimino)-1,2,3-thiadiazoline-2-id, potassium salt × H$_2$O | 0.1 | 25 | 40 |
| | 0.3 | 75 | 75 |
| 5-(phenylcarbamoylimino)-1,2,3-thiadiazoline-2-id, lithium salt × 4 H$_2$O | 0.1 | 35 | 35 |
| | 0.3 | 60 | 60 |
| 5-(N-methylphenylcarbamoylimino)-1,2,3-thiadiazoline-2-id, sodium salt × H$_2$O | 0.1 | 20 | 20 |
| | 0.3 | 50 | 55 |
| 5-(N-methylphenylcarbamoylimino)-1,2,3-thiadiazoline-2-id, potassium salt × H$_2$O | 0.1 | 25 | 20 |
| | 0.3 | 45 | 55 |
| 5-(N-methylphenylcarbamoylimino)-1,2,3-thiadiazoline-2-id, lithium salt × H$_2$O | 0.1 | 30 | 30 |
| | 0.3 | 50 | 50 |
| 5-(2-pyridylcarbamoylimino)-1,2,3-thiadiazoline-2-id, sodium salt × 1.5 H$_2$O | 0.1 | 40 | 35 |
| | 0.3 | 70 | 70 |
| 5-(2-pyridylcarbamoylimino)-1,2,3-thiadiazoline-2-id, potassium salt × H$_2$O | 0.1 | 40 | 40 |
| | 0.3 | 65 | 65 |
| 5-(2-pyridylcarbamoylimino)-1,2,3-thiadiazoline-2-id, lithium salt × H$_2$O | 0.1 | 30 | 30 |
| | 0.3 | 60 | 60 |

EXAMPLE 4

Growing cotton plants in the stage where they have 6 to 8 developed foliage leaves were treated with the agents listed below and the amounts also listed. The amount of water employed was 500 liters per about 2.5 acres. After a few days the percentage of dropped leaves was determined.

TABLE II

| Compound of the Invention | Active agent kg/about 2.5 acres | % defoliation |
|---|---|---|
| 5-(phenylcarbamoylimino)-1,2,3-thiadiazoline-2-id, potassium salt | 0.05 | 69.2 |
| 5-(N-methylphenylcarbamoylimino)-1,2,3-thiadiazoline-2-id, sodium salt | 0.05 | 53.8 |
| 5-(2-pyridylcarbamoylimino)-1,2,3-thiadiazoline-2-id, sodium salt | 0.05 | 73.1 |
| Comparison compound (U.S. Pat. No. 2,954,467) Tri-n-butyl-trithiophosphate | 0.05 | 26.7 |
| | 0.5 | 46.7 |

As it appears from this table the compounds of the invention have a superior activity as against the comparison compound.

EXAMPLE 5

Growing cotton plants in the stage of 7 to 8 developed foliage leaves were treated with the agents and at the amounts appearing from the next table. The amount of water employed was 500 liters per 2.5 acres. After a few days the percentage of the dropped leaves was determined.

TABLE III

| Compound of the Invention | Active agent Kg/about 2.5 acres | % defoliation |
|---|---|---|
| 5-(phenylcarbamoylimino-1,2,3-thiadiazoline-2-id, sodium salt | 0.05 | 76.7 |
| 5-(phenylcarbamoylimino)-1,2,3-thiadiazoline-2-id, potassium salt | 0.05 | 83.3 |
| 5-(2-pyridylcarbamoylimino)-1,2,3-thiadiazoline-2-id, sodium salt | 0.05 | 56.7 |
| 5-(2-pyridylcarbamoylimino)-1,2,3-thiadiazoline-2-id, potassium salt | 0.05 | 56.7 |
| Comparison compound | | |

TABLE III-continued

| Compound of the Invention | Active agent Kg/about 2.5 acres | % defoliation |
|---|---|---|
| (U.S. Pat. No. 2,954,467) Tri-n-butyl-trithiophosphate | 0.05 | 33.3 |
|  | 0.05 | 80.0 |

EXAMPLE 6

Growing cotton plants in the stage where they had 6 to 8 developed foliage leaves were treated with the agents and amounts as appears from the Table IV. The amount of water was 500 l per about 2.5 acres. After a few days the percentage of dropped leaves was determined.

TABLE IV

| Compound of the Invention | Active agent kg/about 2.5 acres | % defoliation |
|---|---|---|
| 5-(phenylcarbamoylimino)-1,2,3-thiadiazoline-2-id, magnesium salt | 0.05 | 78.1 |
| 5-(phenylcarbamoylimino)-1,2,3-thiadiazoline-2-id, zinc salt | 0.05 | 93.8 |
| 5-(phenylcarbamoylimino)-1,2,3-thiadiazoline-2-id, manganese salt | 0.05 | 72.4 |
| 5-(phenylcarbamoylimino)-1,2,3-thiadiazoline-2-id, calcium salt | 0.05 | 87.1 |
| 5-(phenylcarbamoylimino)-1,2,3-thiadiazoline-2-id, barium salt | 0.05 | 93.1 |
| Comparison compound |  |  |
| Tri-n-butyl-trithiophosphate | 0.05 | 18.8 |

EXAMPLE 7

Growing cotton plants in the stage of 7 to 8 developed leaves were treated with the compounds and concentrations appearing from the following Table V. The amount of water was 500 liters per about 2.5 acres. After a few days the percentage of dropped leaves was determined.

TABLE 5

| Components | Amount kg/about 2.5 acres | defoliation % |
|---|---|---|
| 5-(phenylcarbamoylimino)-1,2,3-thiadiazoline-2-id, magnesium salt = I | 0.05 | 33.3 |
|  | 0.1 | 66.7 |
| Magnesium chloride = II | 0.05 | 0 |
|  | 0.1 | 0 |
| I + II | 0.04 + 0.01 | 50.0 |
|  | 0.05 + 0.01 | 63.3 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A compound of the formula

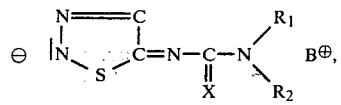

wherein

R$_1$ is hydrogen or C$_1$–C$_4$ alkyl;

R$_2$ is hydrogen, C$_1$–C$_4$ alkyl, C$_5$–C$_8$ cycloalkyl optionally substituted in one or more positions by C$_1$–C$_4$ alkyl, or phenyl, pyridyl or pyrimidyl optionally substituted in one or more positions by the same or different substituents selected from the group consisting of C$_1$–C$_4$ alkyl, C$_1$–C$_4$ alkoxy, C$_1$–C$_4$ alkylthio, halogen, nitro and trifluoromethyl, or R$_1$ and R$_2$ together with the adjoining nitrogen form a morpholino-, piperidino- or pyrrolidino group;

X is oxygen or sulfur; and

B is an alkali metal atom or a univalent zinc, manganese, calcium, magnesium or barium equivalent.

2. The compound of claim 1 wherein the alkali metal atom is a lithium, sodium or potassium atom.

3. The compound of claim 1 which is 5-(phenylcarbamoylimino)-1,2,3-thiadiazoline-2-id, sodium salt×H$_2$O.

4. The compound of claim 1 which is 5-(phenylcarbamoylimino)-1,2,3-thiadiazoline-2-id, calcium salt×8 H$_2$O.

5. The compound of claim 1 which is 5-(phenylcarbamoylimino)-1,2,3-thiadiazoline-2-id, potassium salt×H$_2$O.

6. The compound of claim 1 which is 5-(phenylcarbamoylimino)-1,2,3-thiadiazoline-2-id, lithium salt×4 H$_2$O.

7. The compound of claim 1 which is 5-(methylphenylcarbamoylimino)-1,2,3-thiadiazoline-2-id, sodium salt×H$_2$O.

8. The compound of claim 1 which is 5-(methylphenylcarbamoylimino)-1,2,3-thiadiazoline-2-id, potassium salt×H$_2$O.

9. The compound of claim 1 which is 5-(methylphenylcarbamoylimino)-1,2,3-thiadiazoline-2-id, lithium salt×H$_2$O.

10. The compound of claim 1 which is 5-(2-pyridylcarbamoylimino)-1,2,3-thiadiazoline-2-id, sodium salt×1.5 H$_2$O.

11. The compound of claim 1 which is 5-(2-pyridylcarbamoylimino)-1,2,3-thiadiazoline-2-id, potassium salt×H$_2$O.

12. The compound of claim 1 which is 5-(2-pyridylcarbamoylimino)-1,2,3-thiadiazoline-2-id, lithium salt×H$_2$O.

13. The compound of claim 1 which is 5-(phenylthiocarbamoylimino)-1,2,3-thiadiazoline-2-id, sodium salt×2 H$_2$O.

14. The compound of claim 1 which is 5-(phenylcarbamoylimino)-1,2,3-thiadiazoline-2-id, magnesium salt×2 H$_2$O.

15. The compound of claim 1 which is 5-(phenylcarbamoylimino)-1,2,3-thiadiazoline-2-id, zinc salt×3 H$_2$O.

16. The compound of claim 1 which is 5-(phenylcarbamoylimino)-1,2,3-thiadiazoline-2-id, manganese salt×3 H$_2$O.

17. The compound of claim 1 which is 5-(phenylcarbamoylimino)-1,2,3-thiadiazoline-2-id, barium salt×3 H₂O.

18. A growth regulating composition for plants which includes at least one 1,2,3-thiadiazoline-2-id-derivative as defined in claim 1, the derivative being present in the composition in an amount of about 10 to 80 weight percent and liquid or solid carrier materials being present in an amount of about 90 to 20 weight percent, which composition may also include 20 weight percent of surface active agent in which case there is a corresponding reduction of the carrier materials.

19. A composition as defined in claim 18 which is adapted for defoliation of plants and/or increased formation of off-shoots.

* * * * *